United States Patent [19]

Myer

[11] Patent Number: 4,669,818

[45] Date of Patent: Jun. 2, 1987

[54] MINIATURE WINDOW

[75] Inventor: Jon H. Myer, Woodland Hills, Calif.

[73] Assignee: Hughes Aircraft Company, Los Angeles, Calif.

[21] Appl. No.: 891,069

[22] Filed: Jul. 31, 1986

Related U.S. Application Data

[63] Continuation of Ser. No. 516,814, Jul. 25, 1983, and a continuation-in-part of Ser. No. 226,669, Jan. 21, 1981, abandoned.

[51] Int. Cl.$^4$ .............................................. G02B 6/36
[52] U.S. Cl. ........................... 350/96.20; 350/96.10; 350/96.34; 128/4; 128/398
[58] Field of Search ............... 350/96.18, 96.20, 96.21, 350/96.26, 96.34; 128/395, 4, 6, 398

[56] References Cited

U.S. PATENT DOCUMENTS

| | | | |
|---|---|---|---|
| 2,235,979 | 3/1941 | Brown | 128/6 |
| 3,610,231 | 10/1971 | Takahashi et al. | 128/4 |
| 3,756,688 | 9/1973 | Hudson et al. | 350/96.20 |
| 3,809,072 | 2/1974 | Ersek et al. | 350/96.26 X |
| 4,165,915 | 8/1979 | Rau et al. | 350/96.30 |
| 4,170,997 | 10/1979 | Pinnow et al. | 128/395 |
| 4,253,731 | 3/1981 | Anderson et al. | 350/96.30 |
| 4,266,534 | 5/1981 | Ogawa | 128/6 |
| 4,266,549 | 5/1981 | Kimura | 128/303.1 |
| 4,273,109 | 6/1981 | Enderby | 128/6 |
| 4,375,314 | 3/1983 | Sakuragi et al. | 350/96.29 |
| 4,451,116 | 3/1984 | Pinnow et al. | 350/96.34 |
| 4,552,434 | 11/1985 | Murakami et al. | 350/96.34 |

FOREIGN PATENT DOCUMENTS

| | | | |
|---|---|---|---|
| 0025969 | 4/1981 | European Pat. Off. | |
| 53-5645 | 1/1978 | Japan | |
| 1234958 | 6/1971 | United Kingdom | 350/96.26 |
| 2028530 | 3/1980 | United Kingdom | 350/96.20 |

OTHER PUBLICATIONS

Patent Abstracts of Japan, vol. 2, No. 40, Mar. 16, 1978, p. 271 E 78.

Primary Examiner—William L. Sikes
Assistant Examiner—Akm E. Ullah
Attorney, Agent, or Firm—A. W. Karambelas

[57] ABSTRACT

Fiber optic window (22) has a convergent sealing surface (28), and is pressed into the tapered open end bore of nontoxic sheath (12) which contains toxic fiber optic guide (10) for sealing the sheath. Malleable deformation of the sheath (12) provides hermetic sealing on surface (28). Swaged end of lip portion (36) retains window in place.

10 Claims, 3 Drawing Figures

MINIATURE WINDOW

CROSS REFERENCE

This application is a continuation of application Ser. No. 06/516,814, filed July 25, 1983 and a continuation-in-part of U.S. patent application Ser. No. 226,669, filed Jan. 21, 1981, now abandoned.

BACKGROUND OF THE INVENTION

This invention is directed to a miniature window particularly useful for the hermetic closure of the end of a protective sheath around an optical fiber.

U.S. Pat. No. 4,170,997 to Douglas A. Pinnow and Anthony L. Gentile is directed to a medical laser instrument which employs a flexible fiber optical endoscope which is suitable for application of long wavelength, high power laser radiation for surgical purposes inside the human body. To accomplish this purpose, the toxic, thallium halide optical fiber has a sheath which prevents contact between the body fluid and the fiber optic waveguide material which is capable of infrared transmission. When non-refractory optical fibers are used to transmit long wave infrared radiation, it is often necessary to protect them from a hostile environment and to protect the environment from their toxic effects. For example, fibers of alkali halides, while excellent transmitters of infrared radiation, are very soluble in water and easily corroded by moisture. Some other infrared transparent fibers are made of toxic thallium halides and it becomes necessary to protect the environment from this hazard. It is thus necessary to protect such fibers against body fluids and isolate body fluids from these poisonous substances. In either case, it becomes necessary to surround the fiber with a hermetic protective sheath while providing a means for the radiation to enter or emerge at the end of the fiber.

SUMMARY OF THE INVENTION

In order to aid in the understanding of this invention it can be stated in essentially summary form that it is directed to a miniature window plug which is sealed in the end of a tubular malleable protective sheath for an optical fiber. The window has a conical outer surface which causes malleable outward deformation of the sheath during insertion of the window into the end of the sheath to provide hermetic sealing of the internal volume of the bore of the sheath. The window is transparent to the optical frequency employed.

It is thus an object of this invention to provide a hermetically sealed miniature window and particularly a window assembly suitable for use with very small optic fiber malleable sheaths.

It is another object to provide a method for the hermetic installation of a substantially transparent window plug in the end opening of an optical fiber malleable sheath.

Other objects and advantages of this invention will become apparent from a study of the following portion of the specification, the claims and the attached drawings.

DESCRIPTION OF THE PREFERRED EMBODIMENT

Figure 2:
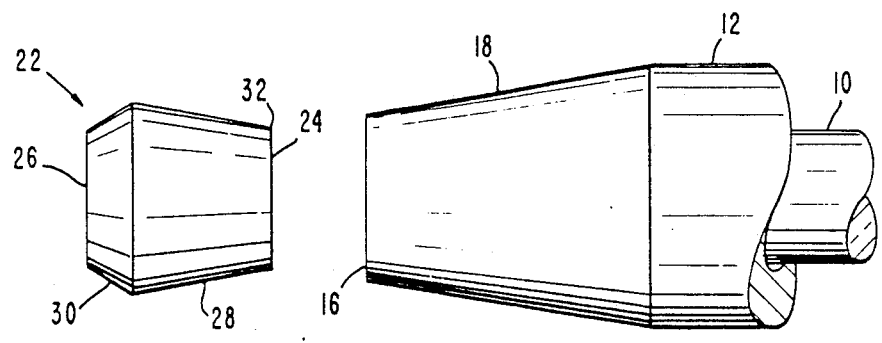
FIG. 2 is a side elevational view of the structure before insertion of the window plug into the end of the bore of the optical fiber sheath.

In the preferred embodiment, optical fiber 10 is substantially transmissive to long wave infrared radiation, and many such fibers are soluble in water, easily corroded by moisture or are physiologically toxic to a human. Examples of suitable alkali halide fibers which are soluble include sodium chloride, potassium chloride and potassium iodide. Examples of toxic fibers are thallium halides, including thallium bromoiodide also known as KRS-5 and thallium bromide. In order to protect the optical fiber 10 against its environment and to protect the environment against the optical fiber 10, physiologically nontoxic sheath 12 is provided.

Sheath 12 is a malleable tubular metallic sheath, for example, a 24 gauge stainless steel or platinum syringe needle tube. Optical fiber 10 is placed therein, with its end 14 recessed with respect to the end 16 of the sheath.

The external surface of sheath 12 is tapered down toward the end 16 to form a right conical surface 18 about the central axis 20 of the entire structure. The conical shaping of the end of the sheath reduces the wall thickness but stops short of forming a knife edge at end 16.

Window 22 is a structure which is physiologically nontoxic and is substantially transparent to the wavelength of interest. For infrared radiation, window 22 can be made of diamond, germanium, zinc selenide or silicon. Window 22 has an axis 20. It has inner and outer planar end facets 24 and 26, both normal to the axis 20. The outer surface of window 22 is comprised of a first convergent sealing surface 28 and a second retaining surface 30. Where the material permits, both of these surfaces are right conical surfaces of revolution about axis 20. The first convergent sealing surface 28 is at the same angle as the original conical surface 18 on the exterior of sheath 12, as seen in FIG. 2. The truncated diameter of surface 28 adjacent the inner planar end 24 is the same as the diameter of the bore 34 of sheath 12.

In materials which are highly crystalline or very hard, or for other reasons cannot form into the desired circular cone, a multifaceted sealing surface 28 can be provided. In some materials, such as diamond such a multifaced surface 28 can be more easily formed. When the window material is diamond a large number of small facets are preferred to minimize sleeve distortion during sealing and to assure a hermetic seal.

Figure 3:
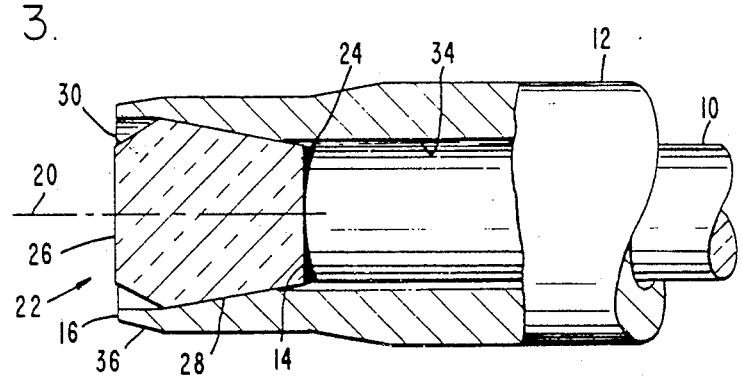
FIG. 3 is a side elevational view, with parts broken away and parts taken in section of the end of the fiber optic sheath, after insertion of the miniature window therein and before final sealing.
Figure 1:
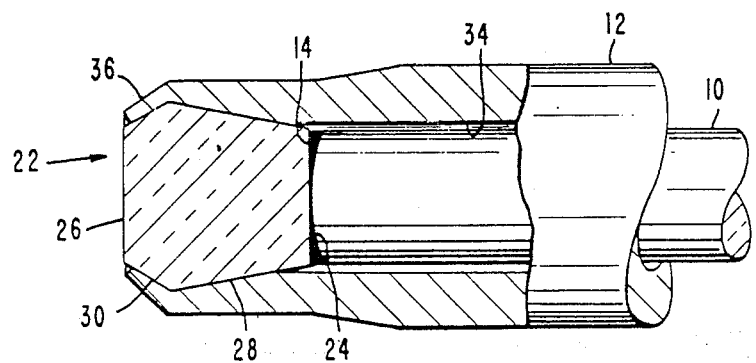
FIG. 1 is a side elevational view of an optical fiber sheath with a miniature window plug therein in accordance with this invention, with parts broken away and parts taken in central section.

As is seen in FIGS. 2 and 3, window 22 is first placed adjacent the open end of sheath 12 and then the first sealing surface 28 is forcibly inserted into the open end of sheath 12. Thrust of the window 22 into the malleable sheath 12 causes expanding deformation of the sheath so that when the window is fully inserted as is illustrated in FIG. 3, the entire sensing surface 28 is in hermetic sealing contact with the sheath. The residual deformation stress causes continued compression of the sheath onto the window on sealing surface 28.

In order to retain window 22 in place, the end portion or lip 36 of the sheath extending over the surface 30 is swaged down onto the surface 30. With the window deforming the bore of the sheath, a hermetic seal is formed, and the window is locked in place by the inwardly swaged end portion of lip 36.

As an aid toward pressing window 22 into the bore, the total included angle of sealing surface 28 was chosen to be 20°, but alternate angles can be employed, as required by the malleability characteristics of sheath 12.

As stated above, suitable materials for window 22 include diamond, germanium, zinc selenide and silicon. These materials have essentially no solubility in fluids with which they might come in contact in a human body and are physiologically nontoxic. All these materials have good transparency in the long wavelength part of the infrared spectrum. All these materials have a large refractive index and thus it is advantageous to provide the window 22 with an anti-reflection coating to maximize transmission. The coating on facet 24 may be any standard coating. However, the coating on facet 26 is exposed to body fluids and must be inert. A multilayer coating such as barium fluoride-zinc selenide will be reasonably resistant to such exposure.

This invention has been described in its presently contemplated best mode and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An optical fiber assembly for use in a biological environment comprising:
    an elongated physiologically toxic optical fiber having ends, said fiber being at least partially transparent to radiation at infrared wavelengths;
    a physiologically nontoxic sheath surrounding said optical fiber adjacent at least one end thereof, said sheath being tubular with a bore therein extending beyond the end of said optical fiber, said sheath being made of malleable stainless steel material, said sheath bore having a swaged divergent interior surface adjacent the end of said sheath; and
    a window within said sheath adjacent said end of said optical fiber, said window being physiologically nontoxic, said window being at least partially transparent to radiation at infrared wavelengths, and having a convergent swaging exterior surface resiliently engaged against and within said divergent swaged interior surface of said sheath bore to hermetically seal and plug the end of said tubular sheath without soldering, said sheath resiliently embracing and engaging said window, said window being at least partially transparent to radiation of the same wavelength to which said optical fiber is at least partially transparent.

2. The fiber optical assembly of claim 1 wherein said divergent bore of said sheath and said convergent surface of said window each comprise two conical surfaces of revolution about an axis centrally positioned through said optical fiber and said sheath respectively and joined together at a common base.

3. The optical fiber assembly of claim 2 wherein said window and said fiber are at least partially transparent to infrared radiation ranging from about 8 to 30 micrometers in wavelength.

4. The fiber optic assembly of claim 1 wherein the end of said sheath extends beyond the convergent external surface of said window to form a lip and said lip is positioned against said window beyond said convergent surface for retaining said window within said sheath and for retaining said convergent surface of said window against said divergent bore surface within said sheath.

5. An optical fiber assembly comprising:
    an elongated toxic optical fiber having ends;
    a nontoxic sheath surrounding said optical fiber adjacent at least one end thereof, said sheath being tubular with a bore therein extending beyond the end of said optical fiber, said sheath being made of malleable stainless steel material, said sheath bore having a swaged divergent interior surface adjacent the end of said sheath; and
    a nontoxic window within said sheath adjacent said end of said optical fiber, said window having a convergent swaging exterior surface engaged against and within said divergent swaged interior surface of said sheath bore to hermetically seal and plug the end of said tubular sheath without soldering, said sheath resiliently embracing and engaging said window, a retaining surface on said window away from said convergent swaging exterior surface in a direction away from said optical fiber, said sheath engaging on said retaining surface on said window to retain said window within said sheath and retain said convergent swaging surface of said window against said swaged divergent bore surface within said sheath.

6. The fiber optic assembly of claim 5 wherein said convergent surface on said window is conical and said retaining surface on said window is a divergent conical surface thereon, said sheath engaging on said divergent surface to retain said window within said sheath.

7. The fiber optic assembly of claim 6 wherein said convergent surface on said window is a truncated right circular cone.

8. The fiber optic assembly of claim 6 wherein said convergent surface on said window is a multifaceted truncated cone.

9. The method of attaching a window plug within the end of a nontoxic malleable tubular sheath having a toxic optical fiber therein comprising the steps of:
    forming the window plug with inside and outside window surfaces thereon and with a divergent surface thereon so that the window surface adjacent the end of the window plug having the smaller cross-section by virtue of the divergent surface forms the inside window surface;
    positioning the window plug with its inside window surface directed toward the end of the malleable tubular sheath; and
    pressing the window plug with its inside window first into the open bore of the tubular sheath so that the divergent surface on the window outwardly forms the malleable nontoxic sheath to produce a resilient hermetically sealed engagement of the sheath onto the window.

10. The method of claim 9 further including the step of plastically deforming the overhanging lip of said tubular sheath around the periphery of the window outwardly of said divergent surface to retain and lock the window within the sheath.

* * * * *